United States Patent [19]

Chandler

[11] Patent Number: 4,839,046

[45] Date of Patent: Jun. 13, 1989

[54] BIO-REACTOR CHAMBER

[75] Inventor: Joseph A. Chandler, Dickinson, Tex.

[73] Assignee: The United States of America as represented by the Administrator of the National Aeronautics and Space Administration, Washington, D.C.

[21] Appl. No.: 87,358

[22] Filed: Aug. 20, 1987

[51] Int. Cl.[4] .................. B01D 29/04; B01D 29/42
[52] U.S. Cl. ............................. 210/355; 210/414; 435/311; 435/316
[58] Field of Search .............. 210/354, 355, 413–415; 435/311, 316

[56] References Cited

U.S. PATENT DOCUMENTS

| | | | |
|---|---|---|---|
| 192,313 | 6/1877 | Watson | 210/355 X |
| 1,000,086 | 8/1911 | Goetz et al. | 435/311 X |
| 2,002,865 | 5/1935 | North et al. | 210/413 X |
| 2,422,735 | 6/1947 | Guardia | 210/355 |
| 2,779,732 | 1/1957 | Knowles | 210/520 |
| 2,889,996 | 6/1959 | Kadden | 210/520 |
| 3,215,274 | 11/1965 | Schreiber | 210/150 |
| 3,275,528 | 9/1966 | Ainis | 435/311 X |
| 3,293,227 | 12/1966 | Boggess et al. | 210/413 X |
| 3,295,686 | 1/1967 | Krueger | 435/311 X |
| 3,618,767 | 11/1971 | Thummel | 210/324 X |
| 3,645,400 | 2/1972 | Floyd | 210/108 |
| 3,840,123 | 10/1974 | McClure | 210/411 |
| 3,853,762 | 12/1974 | Moatti | 210/108 |
| 4,328,317 | 5/1982 | Prentice et al. | 435/316 X |
| 4,347,134 | 8/1982 | Svehaug | 210/147 |
| 4,397,953 | 8/1983 | Guazzone et al. | 435/316 X |
| 4,406,786 | 9/1983 | Hein | 210/223 |
| 4,412,920 | 11/1983 | Bolton et al. | 210/413 X |
| 4,435,505 | 3/1984 | Zierdt | 435/311 X |
| 4,535,062 | 8/1985 | Müller | 435/311 X |
| 4,565,631 | 1/1986 | Bitzer et al. | 210/333.1 |
| 4,649,118 | 3/1987 | Anderson | 435/311 X |

FOREIGN PATENT DOCUMENTS

| | | | |
|---|---|---|---|
| 235989 | 9/1960 | Australia | 210/355 |
| 517251 | 2/1953 | Belgium | 210/413 |
| 590171 | 1/1960 | Canada | 210/413 |

OTHER PUBLICATIONS

"The Large-Scale Cultivation of Mammalina Cells", *Scientific-American*, vol. 248, No. 1, pp. 36–43, Jan. 1983.

*Primary Examiner*—Robert Spitzer
*Attorney, Agent, or Firm*—Edward K. Fein; John R. Manning; Russell E. Schlorff

[57] ABSTRACT

A bio-reactor for cell culture which provides for the introduction of fresh medium without excessive turbulent action. The fresh medium enters the bio-reactor through a filter with a backwash action which prevents the cells from settling on the filter. The bio-reactor is sealed and depleted medium is forced out of the container as fresh medium is added.

5 Claims, 3 Drawing Sheets

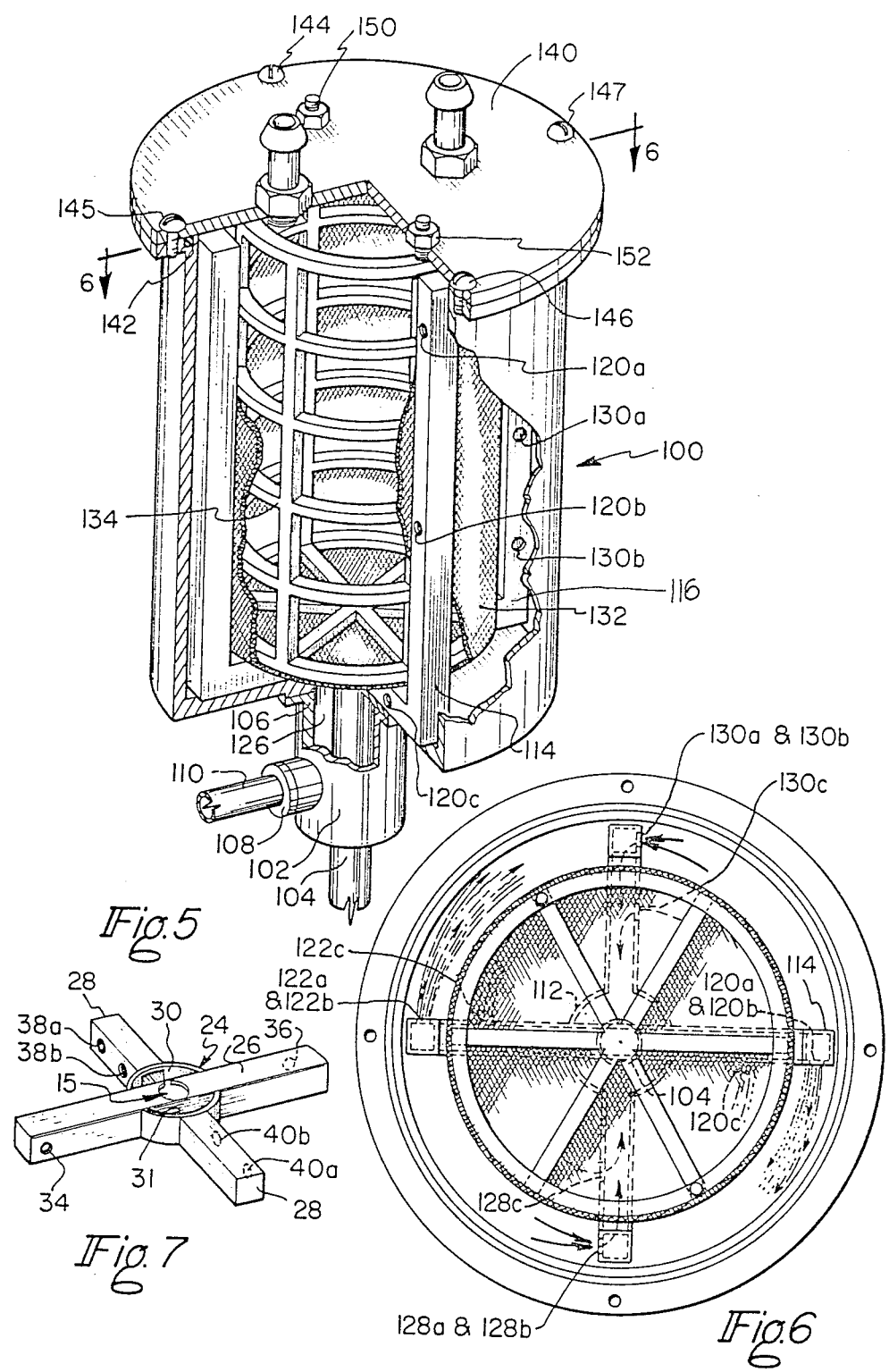

BIO-REACTOR CHAMBER

ORIGIN OF THE INVENTION

The invention described herein was made by an employee of the United States Government and may be manufactured and used by or for the Government of the United States of America for governmental purposes without the payment of any royalties thereon or therefor.

BACKGROUND OF THE INVENTION

Cell culture has developed from the growth of single cell bacteria, yeast and molds which are encased with a tough cell wall to growth of mammalian cells. Mammalian cell culture is much more complex because the cells are more delicate and have a more complex nutrient requirement. Large scale culture of bacterial type cells is well developed and the culture techniques less demanding than mammalian cells. The bacterial cells are grown in large volumes of liquid medium and can be vigorously agitated without any significant damage. Mammalian cells on the other hand cannot withstand excessive turbulent action without damage to the cells and must be provided with a complex nutrient medium to support growth.

In addition, mammalian cells have other special requirements such that most animal cells must attach themselves to some surface to duplicate. On a small scale mammalian cells have been grown in containers with small wells to provide anchors for the cells. The cell culture in the containers with microwells do not provide surface area to grow mammalian cells on a large scale basis. Microcarrier beads were developed which provide surface area for the cultured cells to attach. It can also be placed in a vessel which contains a large volume of culture medium.

A bio-reactor containing microcarrier beads with attached cells must be agitated to provide a uniform suspension in a fresh supply of nutrient. The bio-reactor chambers have internal propellers or agitation devices which are motored driven. The culture vessels contain moving parts within the vessel to cause agitation for the suspension of the mammalian cells on the carrier beads. In addition to propellers, a culture vessel with rotating flexible sheets of nylon have been used. "The Large-Scale Cultivation of Mammalian Cells", *Scientific American*, January 1983, Volume 28, No. 1. pp. 36–43.

The bio-reactors with the internal moving parts cause shearing stress on the cells. The beads collide with each other and damage the cells. The collision of the beads during agitation of the medium in the bio-reactor prevents the usage of high density of microcarriers in the present bio-reactors. One system uses a satellite filter in a separate vessel from the bio-reactor. This is necessary because the microcarrier beads cannot be recycled through the filtering apparatus because the beads are too large to go through the filter pores.

The bio-reactor used to culture mammalian cells utilize mechanical parts which stress the cells. Large numbers of cells cannot be grown due to the impact on the cells.

SUMMARY OF THE INVENTION

The present invention is a simplified bio-reactor which provides a fresh supply of oxygenated fluid nutrient medium into a bio-reactor chamber without excessive turbulence that will cause shear stress on delicate cells. The bio-reactor is designed for culturing mammalian cells but can be used for any type of cell culture.

The fresh nutrient fluid is introduced into the bio-reactor under controlled pressure through a filter. The backwash action on the filter causes cell movement in the medium without the excessive turbulent action that causes the cells to shear. The bio-reactor is sealed. An outlet for depleted medium is provided as the fresh medium is introduced into the bio-reactor. There is a constant exchange of medium. The depleted medium must egress through the filter. The filter pores are sized so that the microcarriers used to culture mammalian cells will not pass through as the medium is exchanged.

The present invention eliminates the mechanical damage to cells due to the impact of rotating agitation or filter components inside a bio-reactor. There is a constant influx and egress of fresh nutrient mixture with low agitation rates to provide for a better mix or suspension. The bio-reactor would provide an environment for increased cell growth with a higher density of microcarriers.

BRIEF DESCRIPTION OF THE DRAWINGS

FIG. 4 is a partial cross-section of the preferred embodiment.

FIG. 5 is a perspective and partial sectional view of an alternative embodiment.

FIG. 6 is a perspective view from the top of the alternative embodiment.

FIG. 7 is a detail of the cross arm structure of the embodiment of FIG. 1.

DESCRIPTION OF THE PREFERRED EMBODIMENT

Figure 1:
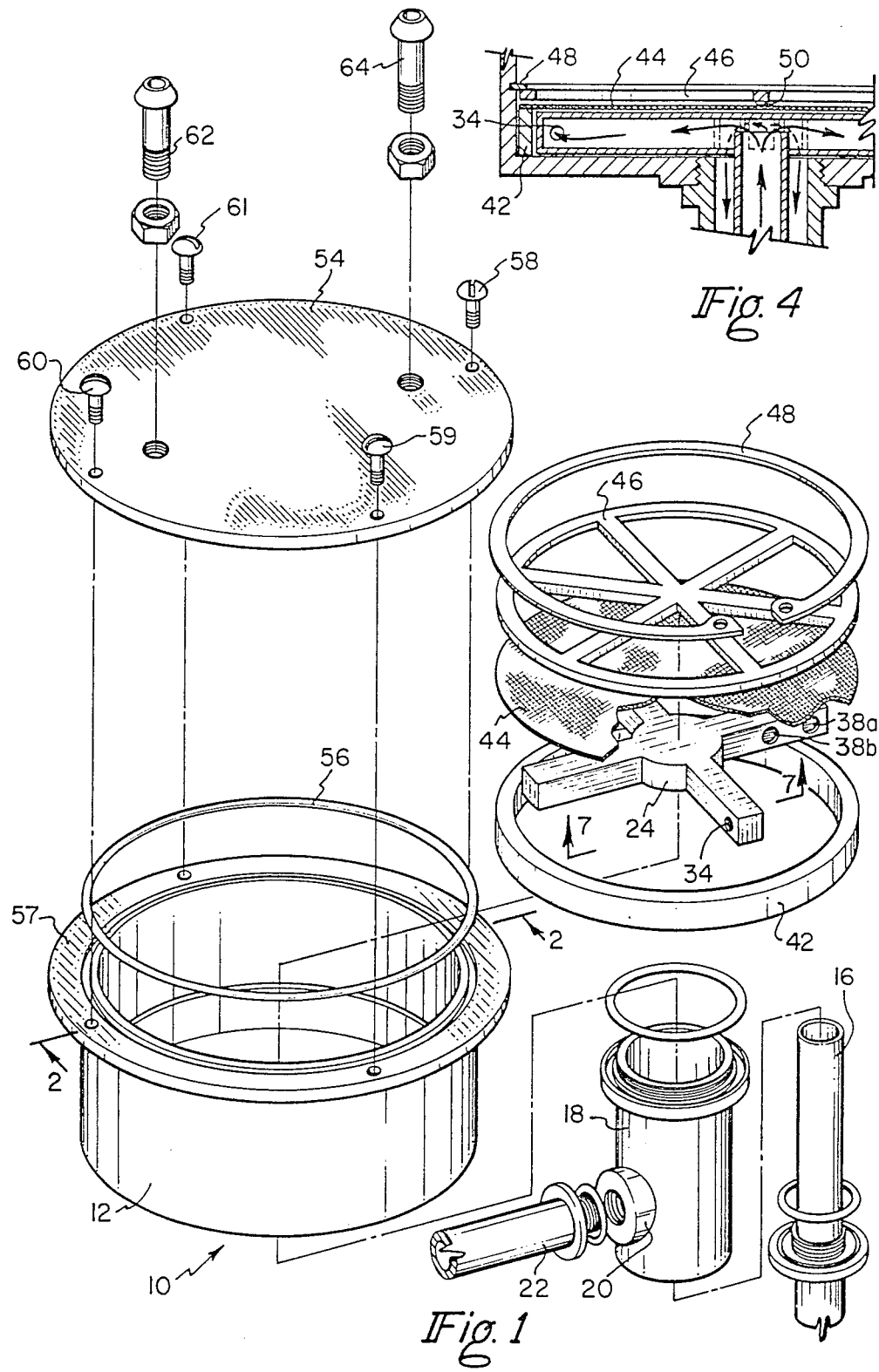
FIG. 1 is an exploded view showing the components of the preferred embodiment.

The drawings illustrate two embodiments of the bio-reactor chamber system with a continuous backwash filter. FIG. 1 is an exploded view of the bio-reactor chamber system which is part of a continuous cell growth system which contains various other component parts which provide oxygenated fresh medium with the proper mix of nutrients. The bio-reactor chamber of the component system is the vessel in which the cells are cultured.

Figure 2:
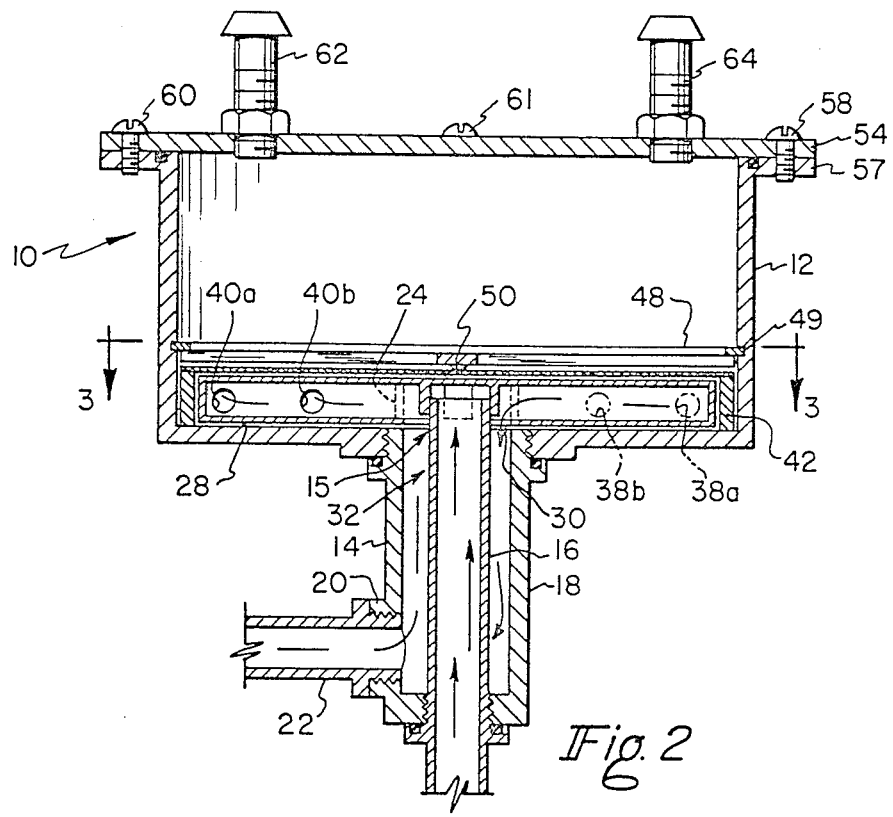
FIG. 2 is a cross-section of the preferred embodiment.

FIG. 2 is a cross-sectional view of the bio-reactor 10. Bio-reactor chamber system 10 has a generally cylindrical short beaker type container 12. The center bottom of the container is attached to a tubular adapter assembly 14. Concentric inlet tube 16 and outlet tube 18 are provided inside tubular adapter 14 with the inlet tube 16 as the central tube extending through the interior bottom of container 12. Outlet tube 18 is a concentric tube which surrounds inlet tube 16. Adapter assembly 14 is provided with a port 20 which communicates with outlet tube 18. Outlet adapter 22 communicates with port 20.

Cross arm structure 24 is disposed in the bottom of the container 12 with the central intersection of the cross arms in the center of the bottom of container 12. The cross arms extend radially from the intersection to the inside perimeter of container 12. The cross arms consist of two hollow pairs of arms lying in the same plane in the bottom of container 12. Inlet cross arm 26 is a hollow construction and extends radially from the intersection of the cross arm sructure 24 from the center of the container. A circular opening is provided in the bottom center of inlet arm 26 through which the inlet tube 16 extends with a very close tolerance providing a bearing surface and seal.

Outlet cross arm 28 is hollow and the outlet arms lie in the same plane as inlet cross arm 26 at a 90 degree angle to the inlet cross arms. Outlet cross arm 28 contains 2 central semicircular openings 30 and 31 in the bottom center of the arm. Openings 30 and 31 are concentric to and surround inlet tube 16 and adjoin outlet tube 18 at the bottom of container 12. Concentric cavity 32 is formed around inlet tube 16 which communicates with hollow outlet arm 28 through semi-circular openings 30 and 31.

FIG. 7 is a detail of the hollow cross arm structure 24 turned upside down to view the opening 15 which receives the inlet tube 16. Also shown are the semi-circular openings 30 and 31 which communicate with the outlet arm 28 to cavity 32. There is no communication between inlet tube 16 extending through opening 15 in the cross arms and the receiving inlet cross arm 26 with the concentric cavity 32 and outlet cross arm 28.

Figure 3:
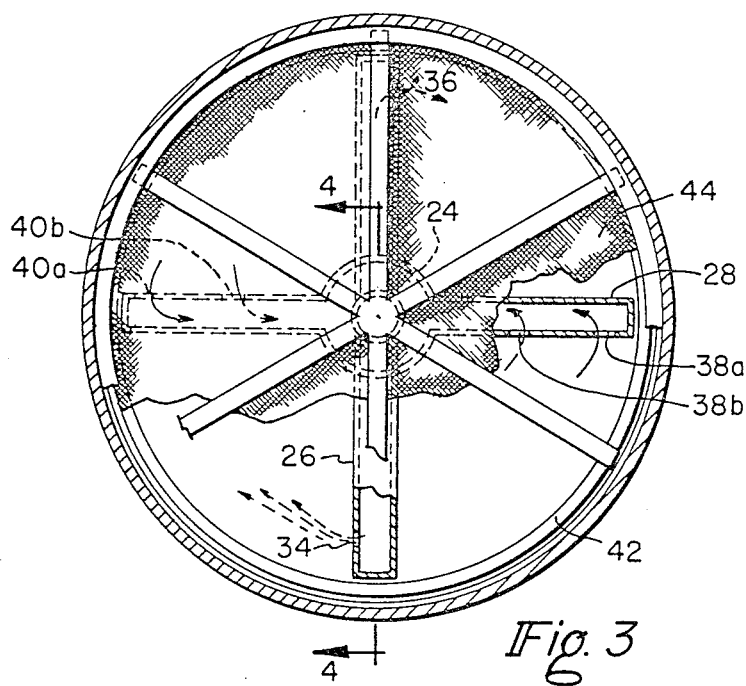
FIG. 3 is a partial section through the cross arm structure of the preferred embodiment.

Inlet cross arm 26 is provided with orifices 34 and 36 on opposite sides of the radially extending arm 26 as shown in FIG. 7. As fluid medium under pressure enters inlet tube 16 and flows into inlet cross arm 26, it is forced out of orifices 34 and 36 causing a rotation of the cross arm structure 24. FIG. 3 and FIG. 7 show the cross arm structure with the inlet cross arm 26 and orifices 34 and 36. The flow of the media is shown out of the orifices 34 and 36 imparting the rotation on cross arm structure 24.

The outlet cross arm 28 contains orifices 38a, 38b, 40a and 40b on the trailing side of the outlet cross arms opposite to the rotational direction caused by the jet action of the emission of fluid medium causing the cross arm structure 24 to rotate. The depleted media goes into orifices 38a, 38b, 40a and 40b.

A spacer ring 42 is shown placed concentric to the bottom interior perimeter of the container 12 and extends the height of the cross arm structure 24. The cross arm structure 24 is fitted with a very close tolerance to spacer ring 42 which allows for rotation of the cross arms 26 and 28 within the spacer ring but does not provide for any more clearance than necessary for the rotation of the cross arms.

A circular filter 44 is bonded to a spider 46 and is disposed just above the cross arm structure 24 in the container 12. The filter can be made of any material compatible with nutrient solution and is typically a fine mesh screen of nylon. The filter is bonded to the spider framework 46 which provides a flexible but secure attachment for the filter. Spider 46 has a spherical bearing surface 50 in the center of the framework which contacts the intersection of inlet cross arm 26 and outlet cross arm 28. The spider 46 bonded to filter 44 is held in place over cross arm structure 24 by a circular retaining ring 48 secured in an interior groove 49 in the side wall of container 12.

Container 12 is provided with lid 54 which is tightly secured with screws 58, 59, 60 and 61 which are shown in FIG. 1. Lid 54 also has a circular sealing ring 56 which contacts lip 57 of container 12 to assure a tight fit. FIG. 1 also shows fill and vent ports 62 and 64 which are typically provided in bio-reactor chambers.

During the operation of the bio-reactor fresh medium is pumped through inlet tube 16 into hollow inlet cross arm 26, out of the orifices 34 and 36 on cross arms causing the cross arm structure 24 to rotate on the bottom of container 12 from the jet action of the fluid passing through the orifices 34 and 36 on inlet arm 26. FIG. 2 shows the ingress of the media through the inlet tube 16. The passage of the media into the outlet arm 28, through openings 30 and 31 to cavity 32 and out of the side outlet adapter 22 is shown in FIG. 2.

FIG. 4 is a cross-section of the inlet cross arm 26 further showing the path of the media. The media flows through inlet tube 16 into the hollow cross arm and out orifices 34 and 36 causing rotation of the cross arm structure. Only orifice 34 is shown in FIG. 4. The media then is forced through the filter 44 into container 12.

During the operation the container 12 is sealed. The medium jetting out of rotating cross arm structure 24 is forced through filter 44 into the main chamber of the bio-reactor where the cultured cells are located. The pores in the filter 44 are sized such that the cells on the microcarriers or otherwise will not pass through the filter 44. As the cross arm 24 rotates from the jet action, the filter 44 is continuously backwashed of any cells which may have settled on the filter.

The jet action disperses the cells in the nutrient medium without internal mechanical action in the main chamber of the bio-reactor. Size of the orifices 34 and 36 can be adjusted for optimum rotational rate to minimize the build-up of cells on the filter, for delivery of medium and proper jet action to maintain an optimum suspension of the cells. As the medium is being pumped into the bio-reactor which is sealed, medium within the reactor or the depleted medium must be displaced. Outlet orifices 38a, 38b, 40a and 40b on outlet arm 28 provide for passage of the depleted medium.

The depleted medium is forced through filter 44, through outlet orifices 38a, 38b, 40a or 40b into the hollow portion of outlet cross arm 28, through concentric outlet cavities 30 and 31 and outlet tube 18 to outlet adapter 22. The depleted medium can be replenished, oxygenated and re-used in the bio-reactor. The size of the outlet orifices can also be optimized to achieve the best results given the size of the container and amount of medium which is pumped through the system.

FIGS. 5 and 6 show an alternative embodiment. The container 100 is generally cylindrical with additional height as compared to the embodiment shown in FIGS. 1, 2, 3, and 4. Container 100 is fitted with a tubular adapter 102 with inlet tube 104 and outlet tube 106 which is concentric with inner tube 104. Adapter 102 is provided with outlet port 108 which is connected to an outlet adapter 110. This arrangement is virtually identical to the other embodiment.

The cross arm structure 112 is composed of a hollow inlet cross arm 114 and hollow outlet cross arm 116. The inlet cross arm 114 and outlet cross arm 116 are hollow, U-shaped in structure and intersect at right angles to each other. The cross arms 114 and 116 intersect at the bottom of the middle of container 100 and extend radially to the perimeter of container 100 and from the perimeter of the container extend up the side of the container to the top edge.

Inlet tube 104 extends through the bottom of container 100 into a circular opening to the center of the bottom of hollow inlet cross arm 114. The inlet tube 104 provides a bearing surface and a seal for the center of inlet arm 114. Inlet arm 114 is provided with orifices 120a, 120b, 120c, 122a, 122b, and 122c. The orifices on inlet arm 114 are generally spaced on the bottom and sides of the structure.

Outlet cross arm 116 is provided with a circular opening on its bottom surface which surrounds inlet tube 104. The opening on the bottom of outlet arm 116 connected to the upper perimeters of outlet tube 106 which extends to the plane of the bottom of container 100. A concentric cavity 126 formed in the adapter 102 below container 100 by the outlet tube 106 surrounding the inlet tube 104. Outlet cross arm 116 is provided with orifices 128a, 128b, 128c, 130a, 130b and 130c on the trailing edge of the outlet cross arm 116.

The filter 132 in the alternative embodiment is bonded to a birdcage spider assembly 134. The filter 132 is generally cylindrical with a circular portion closing the bottom of the cylinder. The filter 132 is generally in the shape of the interior of container 100 and is held against the U-shaped cross arm assembly by the birdcage spider 134. Spider 134 is composed of multiple U-shaped cross arms as shown in FIG. 5 with cross arms connecting the U-shaped sections.

Container 100 has a lid 140 provided with seal 142 and fastened tightly with screw and nut assemblies indicated at 144, 145, 146, and 147. The birdcage spider assembly 134 with bonded filter 132 is held into place with screws 150 and 152.

In operation the alternative embodiment performs in a similar manner to the embodiment described in FIG. 1. The fresh medium enters inlet tube 104 with pressure and is pumped through the U-shaped hollow inlet arm 114. The cross arm structure 112 rotates by the jet action of the fresh medium being forced through orifices 120a, 120b, 120c and 122a, 122b, and 122c on arm 114. Since the container is sealed, the medium inside the bio-reactor is being displaced with fresh medium. The displaced or depleted medium enters the outlet orifices 128a, 128b, 128c and 130a, 130b, and 130c into the hollow portion of outlet cross arm 116 through cavity 126 and further through outlet adapter 110. The pumping of the inlet fluid provides a constant rotation of the cross arm structure providing medium and gentle agitation action to the bio-reactor. The number, size and spacing of orifices on inlet arm 114 depend on the rotational action desired as well as the amount of fresh medium to be provided. The number of orifices or outlet cross arm 116 depends on the need for recycling depleted media.

The materials used for the bio-reactor components are compatible with the bio-reactor systems used for the cell culture. The materials may be selected based on the system used for cell culture taking into account toxicity, durability and maintenance in the culture system. Often Teflon ® or Teflon ® coated metallic parts are used. Other polymer, polymer coated metals or metals can be used depending on the required service.

The bio-reactor of this invention is incorporated in a typical bio-reactor system in place of a bio-reactor that has internal moving parts. The medium introduced would have the proper nutrients and oxygen content. A pump with a pressure control would regulate the inflow of the nutrient in the inlet tube. In a continuous flow system the depleted medium exiting the bio-reactor would be treated for waste removal, reconstituted with the appropriate nutrients and other media requirements, oxygenated and re-introduced into the bio-reactor.

The embodiments described in the specification are not intended to in any way limit the scope of the claimed invention.

What is claimed is:

1. A bio-reactor for cell culture comprising
   a container;
   means to seal the top of said container;
   an inlet for fresh medium into said container;
   an outlet for depleted medium from said container;
   a filter fitted in the inside perimeter of the container;
   liquid medium-driven rotating means disposed within said container below said filter;
   said rotating means including means for delivery of fresh medium from the inlet through the filter into the container causing gentle circulation within the container and causing the filter to continuously backwash with the flow of fresh medium into the container;
   said rotating means further including means for the egress of depleted medium from the container through said filter to said outlet; and
   means retaining said filter adjacent to said means for delivery and said means for egress of medium.

2. A bio-reactor for cell culture comprising
   a generally cylindrical container for culture medium with a central opening in the bottom of the container;
   means to seal the top of said container;
   hollow cross arms in the bottom portion of the container which extend to the perimeter of the interior of the container with the intersection of the radially extending cross arms in the center of the container;
   inlet tube in a central opening in the bottom of the container through which fresh culture medium ingresses the bio-reactor;
   outlet tube concentric to said inlet tube through which depleted medium egresses the bio-reactor;
   one of said hollow cross arms with an opening adjacent the center of the bottom of the container at the intersection of the cross arms which is sized to connect with and communicate with the inlet tube;
   the other of the hollow cross arms with openings adjacent to the bottom of the container at the intersection of the cross arms which is concentric to the inlet tube and connects with the outlet tube;
   a circular filter fitted in the inside perimeter of the container;
   a least one orifice on the cross arm communicating with the inlet tube such that when medium enters into said cross arm pair under pressure a jet action causes the entire cross arm assembly to rotate inside the bottom of the container;
   at least one orifice on each of said cross arm pair communicating with the outlet; and
   means for retaining said filter against said cross arm assembly which allows rotation of said cross arm assembly and the passage of medium into and out of the bio-reactor flowing through the filter.

3. A bio-reactor for all culture of claim 2 wherein said filter is bonded to a spider framework.

4. A bio-reactor for cell culture comprising
   a generally cylindrical container for culture medium with an opening in the bottom of the container;
   means to seal the top of said container;
   hollow U-shaped cross arms which intersect at the bottom portion of said container, extend to the perimeter of the interior of said container and extend upwardly along the sides of the container;

inlet tube in the central opening in the bottom of the container through which fresh culture medium ingresses the bio-reactor;

outlet tube concentric to said inlet tube through which depleted medium egresses the bio-reactor;

one of said hollow cross arms with an opening adjacent the center of the bottom of the container at the intersection of the cross arms which is sized to connect with and communicate with the inlet tube;

the other of the hollow cross arms with openings adjacent to the bottom of the container at the intersection of the cross arms which is concentric to the inlet tube and connects with the outlet tube portion surrounding the inlet tube;

a cylindrical filter with a closed bottom that fits inside the U-shaped cross arms;

a series of orifices spaced on the cross arms communicating with the inlet tube such that when medium enters into said cross arms under pressure a jet action causes the entire cross arm assembly to rotate inside the container;

a series of orifices on each of said cross arm pair communicating with the outlet; and means for retaining said filter adjacent said cross arm assembly which allows for rotation of said cross arm assembly and the passage of medium into and out of the bio-reactor flowing through the filter.

5. A bio-reactor of claim 4 wherein said filter is bonded to a birdcage type framework of intersecting rods forming a cylinder with a bottom.

* * * * *